United States Patent
Li et al.

(10) Patent No.: US 9,401,020 B1
(45) Date of Patent: Jul. 26, 2016

(54) MULTI-MODALITY VERTEBRA RECOGNITION

(71) Applicants: General Electric Company, Schenectady, NY (US); London Health Sciences Centre Research Inc., London (CA)

(72) Inventors: Shuo Li, London (CA); Yungliang Cai, London (CA); Said Osman, London (CA); Mark Landis, London (CA); Manas Sharma, London (CA)

(73) Assignees: London Health Science Centre Research Inc, London, CA (US); General Electric Company, Schenectady, NY (US)

(*) Notice: Subject to any disclaimer, the term of this patent is extended or adjusted under 35 U.S.C. 154(b) by 0 days.

(21) Appl. No.: 14/701,769

(22) Filed: May 1, 2015

(51) Int. Cl.
| | | |
|---|---|---|
| *G06K 9/00* | (2006.01) | |
| *G06T 7/00* | (2006.01) | |
| *G06F 19/00* | (2011.01) | |
| *G06K 9/62* | (2006.01) | |
| *G06T 17/20* | (2006.01) | |
| *G06K 9/48* | (2006.01) | |

(52) U.S. Cl.
CPC .......... *G06T 7/0012* (2013.01); *G06F 19/3437* (2013.01); *G06K 9/481* (2013.01); *G06K 9/6202* (2013.01); *G06T 7/0051* (2013.01); *G06T 17/20* (2013.01); *G06K 2209/05* (2013.01); *G06T 2207/10116* (2013.01); *G06T 2207/30012* (2013.01); *G06T 2207/30204* (2013.01)

(58) Field of Classification Search
None
See application file for complete search history.

(56) References Cited

U.S. PATENT DOCUMENTS

2008/0188734 A1* 8/2008 Suryanarayanan ... G06T 7/0089 600/407

OTHER PUBLICATIONS

T. Klinder et al., "Automated model-based vertebra detection, identification,segmentation in CT images," 2009.*
Zhan et al. ("Robust MR spine detection using hierarchical learning and local articulated model"), 2012.*
Long et al ("Identification and classification of spine vertebrae by automated methods,") 2001.*
Roberts et al ("Automatic location of vertebrae on dxa images using random forest regression,") 2012.*
Zhang et al. ("Automatic construction of parts+geometry models for initializing groupwise registration"), 2012.*
H. Lee, R. Grosse, R. Ranganath, and A. Y. Ng, "Convolutional deep belief networks for scalable unsupervised learning of hierarchical representations," in Proceedings of the 26th Annual International Conference on Machine Learning. ACM, 2009, pp. 609-616.
T. Drummond and R. Cippolla, "Application of lie algebra to visual servoing," International Journal of Computer Vision, vol. 37, No. 1, pp. 21-41, 2000.
J. Ngiam, A. Khosla, M. Kim, J. Nam, H. Lee, and A. Y. Ng, "Multimodal deep learning," in Proceedings of ICML-2011, 2011, pp. 689-696.
N. Srivastava and R. Salakhutdinov, "Multimodal learning with deep boltzmann machines," in Advances in neural information processing systems, 2012, pp. 2222-2230.
G. E. Hinton and R. Salakhutdinov, "Reducing the dimensionality of data with neural networks," Science, No. 5786, pp. 504-507, 2006.

* cited by examiner

*Primary Examiner* — Avinash Yentrapati

(57) ABSTRACT

Systems, methods and computer program products to perform multi-modality vertebrae recognition are provided. Aspects of the present disclosure disclosed and described herein enable a multi-modality vertebrae recognition engine that recognizes vertebrae by using a three-stage recognition approach: landmark detection, global shape registration, and local pose adjustment. These stages cover the matching from local to global spine structures. The three stages are implemented by three modules in the hierarchical deformable model, the local appearance module, global geometry model, and local geometry model. According to one aspect of the present disclosure, the overall workflow can be understood as a three-stage top-down registration. The goal of the registration is: 1) to align the global shape of the spine model, and 2) to align the vertebrae poses with the local image structures around identified landmarks.

15 Claims, 5 Drawing Sheets

MULTI-MODALITY VERTEBRA RECOGNITION

FIELD OF DISCLOSURE

The present disclosure relates to recognition of vertebra structures in radiology images, and more particularly to systems, methods and computer program products to recognize vertebra structures from multiple modalities and using arbitrary views.

BACKGROUND

The statements in this section merely provide background information related to the disclosure and may not constitute prior art.

Automatic spine recognition which supports quantitative measurement is essential in numerous spine related applications in orthopedics, neurology, and oncology. The task of automatic spine recognition is to extract the set of numerical parameters that can uniquely determine the global structure of the spine and certain local structures of the vertebrae. Currently, spine recognition is often simplified as vertebra detection, which extracts the locations and labels of the vertebrae in input images.

Spine recognition is a challenging problem in spine image analysis. In the present application spine recognition is accomplished, in part, by using image appearances. Image appearance is defined as a set of geometric parameters that determine the local and global spine structures. The parameters obtained from spine recognition provides a unified geometry model that can be shared among spine structures from different modalities, different image views, and different formats. The appearance parameters for a spine can be used in quantitative measurement systems for diagnostic purposes and can be stored/retrieved by medical PACS systems. The main difficulties of spine recognition arise from the high variability of image appearance due to modality differences or shape deformations: 1) Multiple modalities. The image resolution, contrast, and appearance for the same spine structure are very different when it is exposed to CT, or T1/T2 weighted MR images. 2) High repetition. The appearances of vertebrae and intervertebral discs are highly repetitive which often leads to mismatching/misrecognition. 3) Various poses. The vertebrae sizes and orientations are highly diverse in pathological data therefore regular detectors such as appearance detectors are insufficient to match all vertebra. 4) Complex shape composition. The spine is composed of local vertebrae and the compositional shape can be highly twisted and cannot be described by simple geometric models like curves and surfaces. Therefore, current methods of recognizing local vertebral structures and global spine shapes are often separately done by spine detection and spine shape matching techniques.

BRIEF SUMMARY

In view of the above, there is a need for systems, methods, and computer program products perform automatic vertebra recognition to identify the global spine and local vertebra structural information such as spine shape, vertebra location and pose. The above-mentioned needs are addressed by the subject matter described herein and will be understood in the following specification.

According to one aspect of the present disclosure, a system that allows automatic vertebra recognition to identify the global spine and local vertebra structural information such as spine shape, vertebra location and pose is provided.

According to another aspect of the present disclosure, a method that allows automatic vertebra recognition to identify the global spine and local vertebra structural information such as spine shape, vertebra location and pose is provided.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

Figure 1:
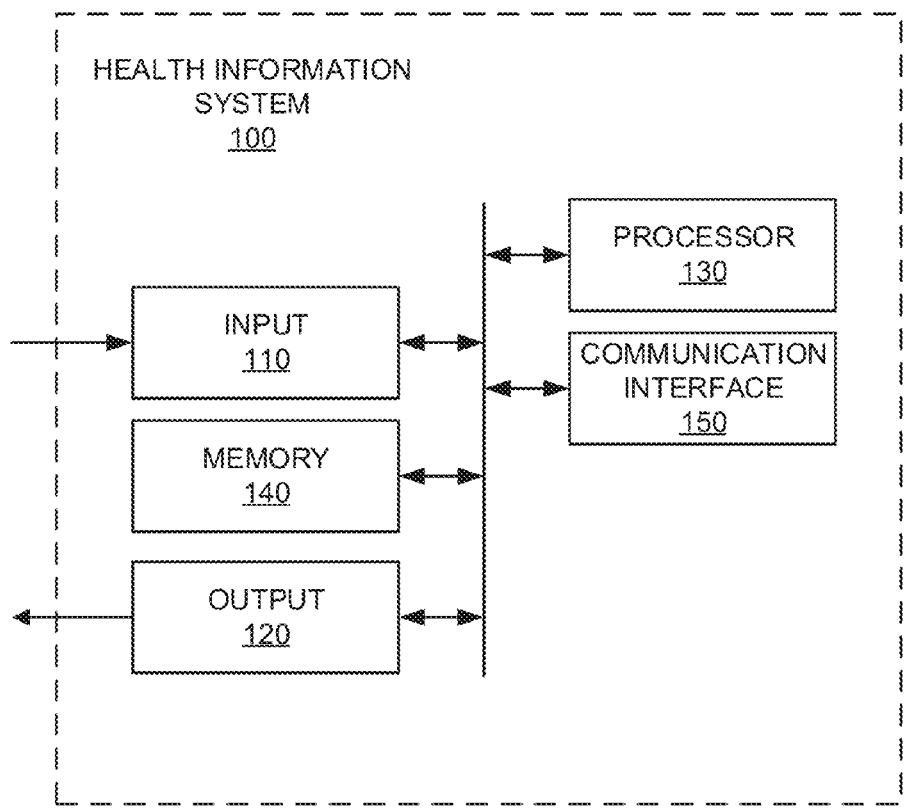
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. OVERVIEW

Aspects disclosed and described herein enable automatic vertebra recognition to identify the global spine and local vertebra structural information such as spine shape, vertebra location and pose. In the present application, a vertebra recognition method using a 3D deformable hierarchical model (DHM) to achieve cross-modality local vertebra location and pose identification with vertebra labeling, and global 3D spine shape recovery is considered.

Other aspects, such as those discussed in the following and others as can be appreciated by one having ordinary skill in the art upon reading the enclosed description, are also possible.

II. EXAMPLE OPERATING ENVIRONMENT

Health information, also referred to as healthcare information and/or healthcare data, relates to information generated and/or used by a healthcare entity. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. Example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

A. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. Example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of example system 100 can be integrated in one device or distributed over two or more devices.

Example input 110 may include a keyboard, a touch-screen, a mouse, a trackball, a track pad, optical barcode recognition, voice command, etc. or combination thereof used to communicate an instruction or data to system 100. Example input 110 may include an interface between systems, between user(s) and system 100, etc.

Example output 120 can provide a display generated by processor 130 for visual illustration on a monitor or the like. The display can be in the form of a network interface or graphic user interface (GUI) to exchange data, instructions, or illustrations on a computing device via communication interface 150, for example. Example output 120 may include a monitor (e.g., liquid crystal display (LCD), plasma display, cathode ray tube (CRT), etc.), light emitting diodes (LEDs), a touch-screen, a printer, a speaker, or other conventional display device or combination thereof.

Example processor 130 includes hardware and/or software configuring the hardware to execute one or more tasks and/or implement a particular system configuration. Example processor 130 processes data received at input 110 and generates a result that can be provided to one or more of output 120, memory 140, and communication interface 150. For example, example processor 130 can take user annotation provided via input 110 with respect to an image displayed via output 120 and can generate a report associated with the image based on the annotation. As another example, processor 130 can process updated patient information obtained via input 110 to provide an updated patient record to an EMR via communication interface 150.

Example memory 140 may include a relational database, an object-oriented database, a data dictionary, a clinical data repository, a data warehouse, a data mart, a vendor neutral archive, an enterprise archive, etc. Example memory 140 stores images, patient data, best practices, clinical knowledge, analytics, reports, etc. Example memory 140 can store data and/or instructions for access by the processor 130. In certain examples, memory 140 can be accessible by an external system via the communication interface 150.

In certain examples, memory 140 stores and controls access to encrypted information, such as patient records, encrypted update-transactions for patient medical records, including usage history, etc. In an example, medical records can be stored without using logic structures specific to medical records. In such a manner, memory 140 is not searchable. For example, a patient's data can be encrypted with a unique patient-owned key at the source of the data. The data is then uploaded to memory 140. Memory 140 does not process or store unencrypted data thus minimizing privacy concerns. The patient's data can be downloaded and decrypted locally with the encryption key.

For example, memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories. Document information may include an identifier, a patient identifier, a clinic identifier, a security category, and encrypted data, for example.

Example communication interface 150 facilitates transmission of electronic data within and/or among one or more systems. Communication via communication interface 150 can be implemented using one or more protocols. In some examples, communication via communication interface 150 occurs according to one or more standards (e.g., Digital Imaging and Communications in Medicine (DICOM), Health Level Seven (HL7), ANSI X12N, etc.). Example communication interface 150 can be a wired interface (e.g., a data bus, a Universal Serial Bus (USB) connection, etc.) and/or a wireless interface (e.g., radio frequency, infrared, near field communication (NFC), etc.). For example, communication interface 150 may communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

B. Example Healthcare Infrastructure

Figure 2:
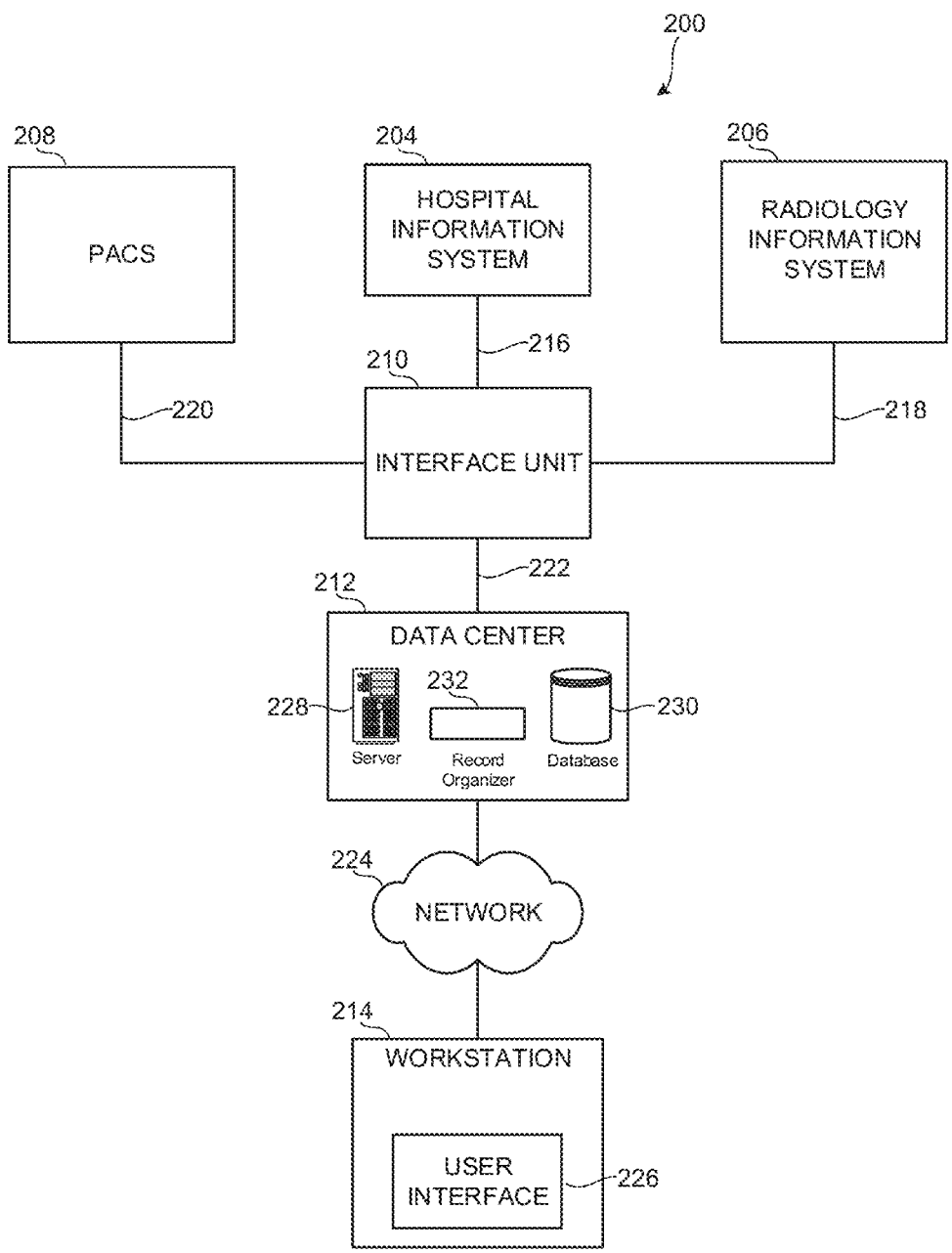
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. Example healthcare system 200 includes a HIS 204, a RIS 206, a PACS 208, an interface unit 210, a data center 212, and a workstation 214. In the illustrated example, HIS 204, RIS 206, and PACS 208 are housed in a healthcare facility and locally archived. However, in other implementations, HIS 204, RIS 206, and/or PACS 208 may be housed within one or more other suitable locations. In certain implementations, one or more of PACS 208, RIS 206, HIS 204, etc., may be implemented remotely via a thin client and/or downloadable software solution. Furthermore, one or more components of the healthcare system 200 can be combined and/or implemented together. For example, RIS 206 and/or PACS 208 can be integrated with HIS 204; PACS 208 can be integrated with RIS 206; and/or the three example information systems 204, 206, and/or 208 can be integrated together. In other example implementations, healthcare system 200 includes a subset of the illustrated information systems 204, 206, and/or 208. For example, healthcare system 200 may include only one or two of HIS 204, RIS 206, and/or PACS 208. Information (e.g., scheduling, test results, exam image data, observations, diagnosis, etc.) can be entered into HIS 204, RIS 206, and/or PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). RIS 206 stores information such as, for example, radiology reports, radiology exam image data, messages, warnings, alerts, patient scheduling information, patient demographic data, patient tracking information, and/or physician and patient status monitors. Additionally, RIS 206 enables exam order entry (e.g., ordering an x-ray of a patient) and image and film tracking (e.g., tracking identities of one or more people that have checked out a film). In some examples, information in RIS 206 is formatted according to the HL-7 (Health Level Seven) clinical communication protocol. In certain examples, a medical exam distributor is located in RIS 206 to facilitate distribution of radiology exams to a radiologist workload for review and management of the exam distribution by, for example, an administrator.

PACS 208 stores medical images (e.g., x-rays, scans, three-dimensional renderings, etc.) as, for example, digital images in a database or registry. In some examples, the medical images are stored in PACS 208 using the Digital Imaging and Communications in Medicine (DICOM) format. Images are stored in PACS 208 by healthcare practitioners (e.g., imaging technicians, physicians, radiologists) after a medical imaging of a patient and/or are automatically transmitted from medical imaging devices to PACS 208 for storage. In some examples, PACS 208 can also include a display device and/or viewing workstation to enable a healthcare practitioner or provider to communicate with PACS 208.

The interface unit 210 includes a hospital information system interface connection 216, a radiology information system interface connection 218, a PACS interface connection 220, and a data center interface connection 222. Interface unit 210 facilities communication among HIS 204, RIS 206, PACS 208, and/or data center 212. Interface connections 216, 218, 220, and 222 can be implemented by, for example, a Wide Area Network (WAN) such as a private network or the Internet. Accordingly, interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with workstation 214, via a network 224, implemented at a plurality of locations (e.g., a hospital, clinic, doctor's office, other medical office, or terminal, etc.). Network 224 is implemented by, for example, the Internet, an intranet, a private network, a wired or wireless Local Area Network, and/or a wired or wireless Wide Area Network. In some examples, interface unit 210 also includes a broker (e.g., a Mitra Imaging's PACS Broker) to allow medical information and medical images to be transmitted together and stored together.

Interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), interface unit 210 translates or reformats (e.g., into Structured Query Language ("SQL") or standard text) the medical information, such as medical reports, to be properly stored at data center 212. The reformatted medical information can be transmitted using a transmission protocol to enable different medical information to share common identification elements, such as a patient name or social security number. Next, interface unit 210 transmits the medical information to data center 212 via data center interface connection 222. Finally, medical information is stored in data center 212 in, for example, the DICOM format, which enables medical images and corresponding medical information to be transmitted and stored together.

The medical information is later viewable and easily retrievable at workstation 214 (e.g., by their common identification element, such as a patient name or record number). Workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. Workstation 214 receives commands and/or other input from a user via, for example, a keyboard, mouse, track ball, microphone, etc. Workstation 214 is capable of implementing a user interface 226 to enable a healthcare practitioner and/or administrator to interact with healthcare system 200. For example, in response to a request from a physician, user interface 226 presents a patient medical history. In other examples, a radiologist is able to retrieve and manage a workload of exams distributed for review to the radiologist via user interface 226. In further examples, an administrator reviews radiologist workloads, exam allocation, and/or operational statistics associated with the distribution of exams via user interface 226. In some examples, the administrator adjusts one or more settings or outcomes via user interface 226.

Example data center 212 of FIG. 2 is an archive to store information such as images, data, medical reports, and/or, more generally, patient medical records. In addition, data center 212 can also serve as a central conduit to information located at other sources such as, for example, local archives, hospital information systems/radiology information systems (e.g., HIS 204 and/or RIS 206), or medical imaging/storage systems (e.g., PACS 208 and/or connected imaging modalities). That is, the data center 212 can store links or indicators (e.g., identification numbers, patient names, or record numbers) to information. In the illustrated example, data center 212 is managed by an application server provider (ASP) and is located in a centralized location that can be accessed by a plurality of systems and facilities (e.g., hospitals, clinics, doctor's offices, other medical offices, and/or terminals). In some examples, data center 212 can be spatially distant from HIS 204, RIS 206, and/or PACS 208.

Example data center 212 of FIG. 2 includes a server 228, a database 230, and a record organizer 232. Server 228 receives, processes, and conveys information to and from the components of healthcare system 200. Database 230 stores the medical information described herein and provides access thereto. Example record organizer 232 of FIG. 2 manages patient medical histories, for example. Record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services.

For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by system 200 via a software-as-a-service (SaaS) implementation over a cloud or other computer network, for example. In certain examples, all or part of system 200 can also be provided via platform as a service (PaaS), infrastructure as a service (IaaS), etc. For example, system 200 can be implemented as a cloud-delivered Mobile Computing Integration Platform as a Service. A set of consumer-facing Web-based, mobile, and/or other applications enable users to interact with the PaaS, for example.

C. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

III. EXAMPLE SYSTEM

Figure 3:
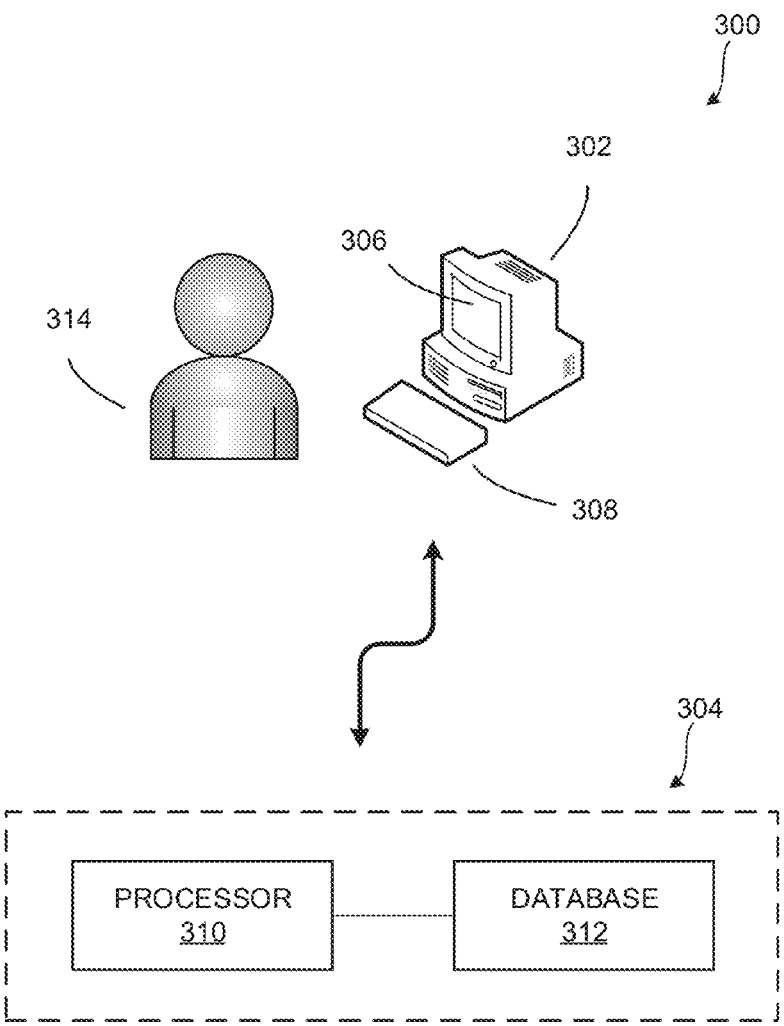
FIG. 3 is a block diagram illustrating an example multi-modality vertebrae recognition engine system, according to the present disclosure.

FIG. 3 depicts an example system 300 for multi-modality vertebrae recognition, according to one aspect of the present disclosure. System 300 includes a computer 302 and a multi-modality vertebrae recognition engine 304 communicatively coupled to computer 302. In this example, computer 302 includes a user interface 306 and a data input (e.g., a keyboard, mouse, microphone, etc.) 308 and multi-modality vertebrae recognition engine 304 includes a processor 310 and a database 312.

In certain aspects, user interface 306 displays data such as images (e.g., spinal images, radiology images, etc.) and/or images containing recognized vertebrae received from regression segmentation engine 304. In certain aspects, user interface 306 receives commands and/or input from a user 314 via data input 308. In aspects where system 300 is used to segment spinal images, user interface 306 displays a spinal image(s) and user 314 provides an initial input identifying, for example, a location of a vertebra boundaries on the spinal image(s).

Figure 4:
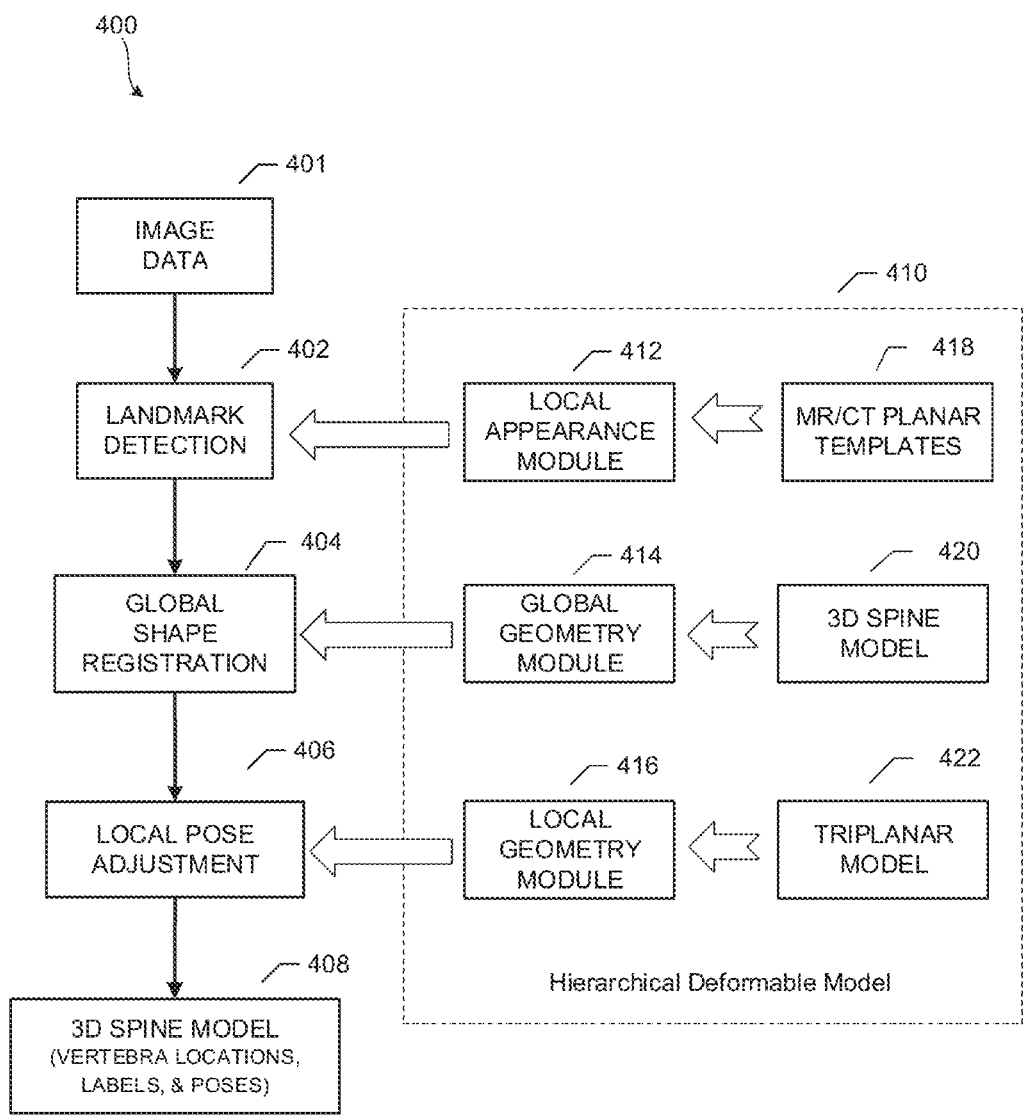
FIG. 4 shows a flow diagram illustrating an example method of operating the system of FIG. 3, according to the present disclosure.

FIG. 4 illustrates a flow diagram of multi-modality vertebrae recognition engine 304 according to one aspect of the present disclosure. In some aspects, multi-modality vertebrae recognition engine 304 generates recognized vertebrae by using a three-stage recognition approach: landmark detection 402, global shape registration 404, and local pose adjustment 406. These stages cover the matching from local to global spine structures. The three stages are implemented by three modules in the hierarchical deformable model 410: the local appearance module 412, global geometry model 414, and local geometry model 416.

According to one aspect of the present disclosure, the overall workflow can be understood as a three-stage top-down registration. The goal of the registration is: 1) to align the global shape of the spine model, and 2) to align the vertebrae poses with the local image structures around identified landmarks.

Landmark detection 402 identifies the potential vertebrae locations from input image data 401. The detection is accomplished by a feature matching between the input image data 401 and the vertebra templates 418. The features used are cross-modality features discussed in more detail below.

Global shape registration 404 aligns the detected landmarks from Landmark detection block 402 with the global spine model 420. Global shape registration 404 abstracts each vertebra as a 3D point so that the registration is completed by a point-based alignment which minimizes the landmark-vertebra point distances. In certain aspects, the registration is formulated as a coherence point drift process and is discussed in more detail below. The aligned spine model provides a coarse identification of vertebrae locations and labels. The 3D vertebrae models are then imposed on the model points.

Local pose adjustment 406 recovers the orientation and dimension of each vertebra. The adjustment determines the optimal alignment between the vertebrae and corresponding image structures, which is accomplished using triplanar model 422 and by a group-wise registration discussed in more detail below. The refined vertebrae are combined to construct a full 3D model of the spine 408. The spine model 408 contains intrinsic labels for each vertebra, thus the registration of the spine model 408 and vertebral landmarks immediately provides the vertebra detection and labeling.

IV. EXAMPLE METHOD

Basic Models

Triplanar Model.

The triplanar model is designed for the joint representation of 3D shape and 3D appearance of a vertebra. In certain aspects, each triplanar vertebra model contains a 3D mesh model embedded with a triplanar template representation. The three planar templates in this model are three MR or CT patches describing the MR/CT appearance of a 3D vertebra projected on coronal, sagittal, and axial views, respectively. The detection of a vertebra landmark in an image is accomplished by searching of identical matching between the planar templates and the input image. In addition, the 2D warping of a planar template on the associated image plane is considered as applying a 3D deformation for the 3D vertebra model then projecting the appearance on that image plane.

3D Spine Model.

The spine model used in global shape recognition 404 is built upon a 3D spine mesh model. The meshes are manually built from CT scans of a healthy spine. In certain aspects, each vertebra in the 3D spine mesh is individually built and manually assigned to construct the corresponding MR or CT triplanar vertebral model 422. In certain aspects, the meshes assigned and the corresponding triplanar templates 418 are aligned using 3D CAD software. The resulting meshes can be applied to both MR and CT matching as the obtained anatomic structure is independent to image modality. The 3D spine model 420 and the associated triplanar vertebra 422 are assigned with different deformation mechanisms and are unified in the Hierarchical Deformation Model 410.

Hierarchical Deformable Model

Hierarchical Deformable Model (HDM) 410 is used for the deformable matching of local/global spine structures. Combining triplanar vertebra models 422 under the organization of a 3D spine constructs a compositional structure that simulates the spine anatomical deformation mechanism for spine matching. The model contains three modules:

1) Local appearance module 412 contains the planar templates 418 for each vertebra in each view. The templates are described by cross-modality features which unifies the appearances of both MR and CT. This module conducts the landmark detection using the planar templates 418.

2) Local geometry module 414 contains the triplanar vertebra models 422 composed by the planar templates 418 from local appearance module 412. Local geometry module 414 conducts pose adjustment for each vertebra via the warping of planar templates 418. The warping is guided by the groupwise registration (joint-alignment) of the planar templates 418.

3) Global Geometry Module 416 contains the set of connected triplanar vertebra models 422 organized under the spatial layout of a spine. This module conducts shape registration between detected landmarks from block 402 and the built-in vertebra models 420. The registration is implemented by a point-based registration process which aligns the abstracted vertebra points with the landmark points.

The advantages of using the hierarchical model includes: 1) weak supervision. HDM 410 borrows geometric deformation in handling vertebra detection so that training sophisticated vertebra detectors is no longer necessary. This solves the shortcomings of most learning-based methods, where a large number of samples and intense manual labeling is required in the training stages. 2) Versatile data adaptation. The triplanar representation can perform spine recognition on both specified MR/CT slices and whole image volume. User not only can obtain the recognition result significantly faster, but also can control the progressive spine shape approximation by feeding the model with more/less slices. 3) 3D reconstruction as a natural by-product. The spine detection and matching directly correspond to the deformations of a standard 3D spine model, which in turn, provides a model-based 3D reconstruction of the spine image.

Local Appearance Module for Vertebra Landmark Detection

Local appearance module 412 is used for extracting cross-modality features that robustly encode the vertebra appearances in different image modalities. The cross-modality features are obtained by fusing the image features from MR and CT using a multi-model deep network. Using the fused features, the vertebra landmark detection can be performed on both MR and CT data with improved accuracy.

Feature Extraction Using Multi-Modal Deep Networks

A multi-modal deep network model is applied for learning and extracting features across modalities. Cross-modality features are more reliable than single modality features in vertebra detection because some image structures in one modality will be nearly missing in another modality, i.e., vertebra discs features in MR scans will be missing in CT scans. Thus, single modality features from either MR or CT will be insufficient to describe the complete vertebra structure. Also, features from different modalities tend to compensate and enhance each other; for example, disc features from MR can help to identify the vertebra locations for CT scans as discs and vertebrae share a lot common image structures (i.e., vertebrae boundaries). Therefore, good vertebra features can be learned by fusing image features from all presenting modalities.

Network Design.

In certain aspects of the present disclosure, the multi-modal network design is different from previous work by building the network on two convolution restricted Boltzmann machine (CRBM) layers and two layers of restricted Boltzmann machine (RBM). Through the layer-wise iterative update of convolution filter-banks, the CRBMs adaptively extract significant 2D image features. For each image modality, a unique set of CRBMs is used for extracting translation-invariant features from that modality. Similar to CRBM, through a layer-wise update of their connecting weights, the RBMs provide a well-ordered representation of the input signals. Unlike single-modal training, in certain aspects of the present disclosure, the upper layer RBMs are trained by feeding them the extracted lower-layer MR and CT features together. The RBMs automatically mix the MR and CT features generating a unified representation for both MR and CT modalities. The complete learning process is conducted in an unsupervised fashion.

Feature Fusion.

Feature fusion is a unique property of deep network models. The purpose of feature fusion is to combine the common features shared among different modalities and to enhance the feature representation for capturing more image details. Traditional learning-based detection methods often rely on the direct classification of handcrafted features such as SIFT, HOG, or Haar functions. Because of the distinct appearances of original image modalities, the corresponding feature maps of the handcrafted features can be extremely diverse. The supervised classifiers will require a large amount of labeled data to resolve this diversity. In contrast to traditional methods, deep networks contain multi-layer abstraction and adaptive features tuning that automatically combine the higher layer feature representation of different modalities. These combinations also enhance the single modality features extracted from lower layers as the combined features can now represent additional image structures from other modalities, i.e., a better MR feature can be learned by using CT samples and vice versa. Therefore, the multi-modal deep network requires less training samples than the traditional approaches but still can obtain good discriminative features.

Configurations.

In certain aspects, the parameters of the deep network are as follows. Layer 1 CRBM consists of a 7×7×6 filter-bank and layer 2 CRBM consists of a 9×9×12 filter-bank. Each filtering is followed with a ½ sub-sampling and probability pooling. The resulting output of layer 2 is a 72-dimensional binary feature map with each map becoming ¼ of the original image. Layer 3 will map each 6×6×72 cube in layer 2 to a feature vector of 800 dimensions. The last layer (layer 4) will reduce the dimensions of the layer 3 vector to 200 dimensions. The final deep feature map is a 200-dimensional map where each map is of ¼ the original image size. i.e., every 24×24 image patch is encoded to a 200 descriptor vector through the network. In certain aspects, the CRBMs and RBMs are learned through a training set which contains 50 T1 MR slices, 50 T2 MR slices, and 100 CT slices. In certain aspects, all slices are sampled near the mid-plane in the image volume with the same size of 250×250, as pixel size is 1×1 mm. The MR features and CT features are separately learned then fused by the RBM layers.

Planar Template Construction

The planar appearance template used in landmark detection are the MR/CT template patches 418 in triplanar vertebra model 422. A planar template is generated by taking the mean of a set of training patches from different image slices, then map the mean patches to high dimensional feature map using the deep network. For example, the sagittal template of the lumbar vertebrae in CT is generated by taking the mean appearance of the set of lumbar image patches in the CT training set then convert it to feature maps. Note that in certain aspects, the training images are aligned beforehand by using the part-based registration model discussed below. In certain aspects, there are four different types of templates: lumbar (L), thoracic (T), cervical (C), and sacrum (S). Each template type is generated separately by the same approach. In certain aspects, there are a total of 4×2×3 templates that serve the four vertebra types (S, L, T, C), two image modalities (MR and CT), and three views (coronal, sagittal, and axial). Once the input image modality is identified from the image header, the associated templates are loaded in the triplanar model to perform the appearance matching.

Templates Vs Trained Classifiers.

The reason for choosing the template approach is that the invariant appearance of a vertebra pattern is unique to other local image appearances and most of the mismatching is caused by pose distortions. It is more efficient to discriminate vertebrae from local image structures using the invariant vertebra appearance along with pose deformations. Previous supervised learning-based detection methods focus on vertebra appearance only and resolve pose variations by training their classifiers with extra samples, especially large amount of pose varied samples. The use of planar template with unsupervised learned features and pose deformations not only reduces the workload of collecting large amounts of medical data with massive manual labelling, but also significantly simplifies the training process while still maintaining the performance of vertebrae detection.

Landmark Detection

The initial landmark detection is done by matching the vertebra appearance templates with the input image. The trained deep network is applied in this detection. According to the input image modality, layer 1 and 2 in the deep network is substituted with the related MR/CT CRBMs, and with RBM layers remained unchanged. Following the filtering and pooling process of the deep network, the input image slice is expanded to a set of high-dimensional feature maps.

Detection.

Using the deep-feature descriptor mentioned above, the template matching is done by comparing the $L^2$ distances of the feature vectors between input image and the appearance template. Suppose $f_{dp}$ is the deep feature descriptor defined by the deep network, for a template T the matching response on point p in an input image I is:

$$r(p,T)=\exp(-\epsilon\|f_{dp}(I_p)-f_{dp}(T)\|^2) \qquad \text{Equation 1:}$$

where $I_p$ is the image patch centered at p with the same size of T and c is a fixed constant.

The template T is deformed with a set of transforms $\mathcal{G}$ to match different vertebrae with various poses. In certain aspects, $\mathcal{G}$ can be a series of 2D rotations and re-scalings. After the basic matching for each input scan I, responses are synthesized for their corresponding image views and obtain the final 3D responses. The peak positions are the desired vertebra landmarks. Finer positioning is obtained by using a pose adjustment for each landmark as discussed below.

Local Geometry Module for Vertebra Pose Adjustment

The goal of the local geometry module is to estimate the 3D pose of each triplanar model for the best model-image alignment. In certain aspects, the pose of a triplanar vertebra model is defined as the orientation and the anisotropic scales of that model in 3D space. The 3D pose can be described by the projections of 3D vertebra on 2D planes, which is equivalent to the planar poses of the intrinsic templates from the triplanar model. The optimal 3D poses of the collected triplanar models are obtained by a group-wise registration of the planar templates, and then by the back-projections of the planar poses to 3D.

Planar Pose Representation

The planar pose of a triplanar vertebra model 422 is the 2D orientation and sizes of its three built-in planar templates. Due to the rigidity of vertebra model, the planar poses are defined as invertible 2D affine transforms. The invertibility of pose transforms implies that any arbitrary planar pose can be generated from one reference pose. In certain aspects, this assumption is used in estimating the planar poses of each triplanar vertebra model.

Generative Model.

For a given image view, e.g., sagittal view, the vertebra patterns that appear on the input slices are assumed to be generated by the same appearance template. The reference template is from the sagittal template patch of a triplanar model. According to repetition of vertebra patterns, we assume that each spine section (sacrum, lumbar, thoracic, and cervical) has its own reference appearance. Different vertebrae in the same section differ only by their poses. For example, a template of sagittal CT lumbar generates the repetitive lumbar vertebra patterns in sagittal CT slice with varied poses. Let $T \in \mathbb{R}^{d_1 \times d_2}$ be the planar template, $d_1$ and $d_2$ are the height and width of the template patch. The potential vertebra landmarks p on an arbitrary slice I satisfies:

$$T \circ G_p = I_p \quad \text{Equation 2:}$$

where $I_p$ is the local vertebra patch with arbitrary pose, and $G_p$ is a geometric transform that warps T to $I_p$ so that T 'generates' $I_p$ via $G_p$. Stitching a set of deformed template replicas together can reconstruct the spine appearance.

Pose Geometry.

2D transforms are defined on planar poses by an algebraic model. According to the generative model, the planar pose of a vertebra at p is uniquely determined by transform $G_p$. The $G_p$ is defined as an affine transform which can be explicitly formulated as a 3×3 invertible transform matrix. All possible transform matrices form a Lie group $Aff(2) \subset GL(3)$. Using the matric group form, $G_p \in Aff(2)$ is formulated as:

$$G_p = \text{Exp}(\Sigma_{k=1}^{6} a_p^{k} E_k) \quad \text{Equation 3:}$$

$$E_1 = \begin{pmatrix} 1 & 0 & 0 \\ 0 & 1 & 0 \\ 0 & 0 & 0 \end{pmatrix} \quad E_2 = \begin{pmatrix} 1 & 0 & 0 \\ 0 & -1 & 0 \\ 0 & 0 & 0 \end{pmatrix} \quad E_3 = \begin{pmatrix} 0 & -1 & 0 \\ 1 & 0 & 0 \\ 0 & 0 & 0 \end{pmatrix} \quad \text{Equation 4}$$

$$E_4 = \begin{pmatrix} 0 & 1 & 0 \\ 1 & 0 & 0 \\ 0 & 0 & 0 \end{pmatrix} \quad E_5 = \begin{pmatrix} 0 & 0 & 1 \\ 0 & 0 & 0 \\ 0 & 0 & 0 \end{pmatrix} \quad E_6 = \begin{pmatrix} 0 & 0 & 0 \\ 0 & 0 & 1 \\ 0 & 0 & 0 \end{pmatrix}$$

where $a_p = [a_p^1, \ldots, a_p^6]$ and the infinitesimal generators $\{E_k\}$ form the Lie algebra aff(2) of Aff(2). The deformations on planar templates on different views will determine a 3D pose of the 3D vertebra model. This allows for the estimation the 3D pose through 2D methods as 2D models can be directly applied on single/multiple slice data or volume data.

The Lie group formulation is adopted by the model since the pose changes between adjacent vertebrae are smooth. Also, the planar deformations are considered to be smooth in local vertebra set and during the deformation process. This formula conforms to the kinematics model for robotics, where the continuous deformations on rigid structure are represented by smooth matrix groups. The pose of a planar template is parameterized by the 6 parameters in vector $a_p$. The pose of the associated 3D vertebra are controlled by 18 parameters, which correspond to the three degrees of freedom on sagittal, axial, and coronal views.

Planar Pose Adjustment by Group-Wise Registration

The recovery of template pose is accomplished by aligning the planar template to the identified landmark in the image. This can be understood as solving Equation 2 for landmark patch $I_p$ when $G_p$ is unknown. In addition, because of the repetitions of vertebra appearances, the alignment is not only applied on the landmark-template pairs but also between landmark pairs. The landmark-landmark alignment helps to enhance the regularity of landmark patches and reduce the ambiguity of the landmark identification. In certain aspects, a part-based group-wise registration is applied for regularizing the landmark detection using the vertebra repetition. The registration model is a variant of a congealing model. However, unlike the congealing model the proposed model is part-based and can be applied on repetitive image patches.

Mathematical Formulation.

Given a set of sampled scans from the same image view, an initial landmark set $\mathfrak{T}$ is identified such that $I_p$ is a deformable landmark patch observed on $p \in \mathfrak{T}$, p is represented as the planar coordinates of the image view. Suppose T is the corresponding template for the identified landmarks, then the alignment is formulated as the minimization of the function:

$$u(G_p) = \phi_T(G_p) + \Sigma_{(p,q) \in \mathcal{N}} \psi(G_p, G_q) \quad \text{Equation 5:}$$

where $\phi$ is a data term and $\psi$ is a smoothness term for neighbor set $\mathcal{N}$. Let $I_p \circ G_p^{-1}$ and T be vectors in $\mathbb{R}^{d_1 \times d_2}$, $\phi$ and $\psi$ are then defined as:

$$\phi_T(G_p) = \|I_p \circ G_p^{-1} - T\|^2 \quad \text{Equation 6:}$$

$$\psi(G_p, G_q) = \|I_p \circ G_p^{-1} - I_q \circ G_q^{-1}\|^2. \quad \text{Equation 7:}$$

The expression of $I_p \circ G_p^{-1}$ means the deformed landmark patch $I_p$ is warped by transform $G_p^{-1}$ to exactly the same size of T. In other words, $I_p \circ G_p^{-1}$ and $I_q \circ G_q^{-1}$ are of the same size such that direct subtraction is possible. To make the registration more robust, certain aspects encode the patch by the deep feature descriptor described above. Each landmark patches become a feature patch written as $f_{dp}(I_p \circ G_p^{-1})$. Note that $G_p$ is parameterized by $a_p$, and is written: $F_p(a_p) = f_{dp}(I_p \circ G_p^{-1})$. Therefore, for a $\lambda_u > 0$, Equation 5 becomes a functional variable $a_p$ as $$u(a_p) = \phi_T(a_p) + \Sigma_{(p,q) \in \mathcal{N}} \psi(a_p, a_q) \quad \text{Equation 8:}$$

$$\phi_T(a_p) = \|F_p(a_p) \circ G_p^{-1} - f_{dp}(T)\|^2 \quad \text{Equation 9:}$$

$$\psi(a_p, a_q) = \|F_p(a_p) - F_q(a_q)\|^2. \quad \text{Equation 10:}$$

In certain aspects, the functional u is solved by Gauss-Newton method, with the alignment being taken over each p in sampled image scans. The pose change $\Delta a_p$ is obtained via $$\Delta a_p = (J^T J)^{-1} J^T d(a) \quad \text{Equation 11:}$$

$$d(a) = F_p(a_p) - f_{dp}(T) + \Sigma_{(q,p) \in \mathcal{N}} (F_p(a_p) - F_q) \quad \text{Equation 12:}$$

$$J(a_p) = \left( \frac{\partial d(a_p)}{\partial a_p^1}, \ldots, \frac{\partial d(a_p)}{\partial a_p^k} \right)^T \quad \text{Equation 13}$$

The coefficient vector $a_p$ is iteratively updated: $a_p + \Delta a_p$, leading to the progressive alignment of the vertebra parts. The updated $a_p$ is substituted back into equation 3, warping the planar temple and the 3D vertebra. In certain aspects, the part-based registration can be applied on landmark patches within a single image scan or those distributed among multiple scans. This allows for the conducting the registration on arbitrary image views as some repetitions do not appear in the single image.

Estimation of 3D Pose

Through the group-wise registration on different image views, the planar pose of each potential landmark patches are described by the optimal vector $a_p$ obtained by equation 8. The planar poses are then back-projected from three views (coronal, sagittal, axial) to synthesize a 3D pose so that the dimensions and orientation of a triplanar vertebra model are fully recovered. The estimation problem is similar to that found in visual serving, where the 3D transform is recovered by projection 2D planar deformations.

From Aff(2) to SE(3).

The 3D vertebra model is a rigid structure whose pose is defined by an invertible 3D rotation and a translation. This is a different assumption from that if the planar template assumption as the planar template is allowed to both rotate and dilate under affine transforms. For a potential landmark, which is identified in three image views, let p denote the landmark center. The possible 3D transforms form a Lie group SE(3) such that $R_p \in SE(3)$ is a 4×4 transform with a matric group representation similar to equation 3:

$$R_p = \text{Exp}(\Sigma_{k=1}^{6} c_p^k V_k) \quad \text{Equation 14:}$$

Equation 15

$$V_1 = \begin{pmatrix} 0 & -1 & 0 & 0 \\ 1 & 0 & 0 & 0 \\ 0 & 0 & 0 & 0 \\ 0 & 0 & 0 & 0 \end{pmatrix} \quad V_2 = \begin{pmatrix} 0 & 0 & 1 & 0 \\ 0 & 0 & 0 & 0 \\ -1 & 0 & 0 & 0 \\ 0 & 0 & 0 & 0 \end{pmatrix} \quad V_3 = \begin{pmatrix} 0 & 0 & 0 & 0 \\ 0 & 0 & -1 & 0 \\ 0 & 1 & 0 & 0 \\ 0 & 0 & 0 & 0 \end{pmatrix}$$

$$V_4 = \begin{pmatrix} 0 & 0 & 0 & 1 \\ 0 & 0 & 0 & 0 \\ 0 & 0 & 0 & 0 \\ 0 & 0 & 0 & 0 \end{pmatrix} \quad V_5 = \begin{pmatrix} 0 & 0 & 0 & 0 \\ 0 & 0 & 0 & 1 \\ 0 & 0 & 0 & 0 \\ 0 & 0 & 0 & 0 \end{pmatrix} \quad V_6 = \begin{pmatrix} 0 & 0 & 0 & 0 \\ 0 & 0 & 0 & 0 \\ 0 & 0 & 0 & 1 \\ 0 & 0 & 0 & 0 \end{pmatrix}$$

For a triplanar vertebra model, the three template patches inside the model is rotated and translated according to the pose of the 3D vertebra, i.e., the warped planar landmark obtained from group-wise registration is the projection of the corresponding template patch in the vertebra model. The corners of the built-in three template patches define a 3D bounding box for the 3D vertebra model. The template-landmark projection indicates that the projections of the 3D corners also define the warped bounding boxes of the planar landmarks. Utilizing the 2D-3D projection between corners, the 3D pose of the vertebra model is recovered.

Estimation Formulation.

Let $p_s$ be the 3D corner of the sagittal template patch in the triplanar vertebra model. The orthographic projection $P_s$ such that $P_s p_s$, is the 2D corner of the warped landmark bounding box on the projected sagittal image plane. The projection of sagittal corners, axial corners, and coronal corners respectively as $\hat{p}_s, \hat{p}_a, \hat{p}_c$ $$\hat{p}_s = P_s p_s$$

$$\hat{p}_a = P_a p_a$$

$$\hat{p}_c = P_c p_c \quad \text{Equation 16:}$$

Note that any 3D corner $p$ and 2D corner $\hat{p}$ in the above equations are represented in homogeneous coordinates, and projection P is a 4×4 matrix which agrees with the matrix definition in equation 14. In certain aspects, the initial positions of the 3D corners are $P_{s0}, P_{a0}, p_{c0}$, the relations of the template-landmark projection is described as $$e(c) = \sum_{i=1}^{4} \|P_S R p_{s0}^i - \hat{p}_s^i\|^2 + \|P_a R p_{a0}^i - \hat{p}_a^i\|^2 + \|P_c R p_{c0}^i - \hat{p}_c^i\|^2 \quad \text{Equation 17}$$

where $p^1, \ldots, p^4$ represent the four corners of the template patch. $\mathcal{R}^*$ is the desired 3D pose such that $$\mathcal{R}^* = \arg\min_{\mathcal{R} \in SE(3)} \{e(\mathcal{R})\} \quad \text{Equation 18}$$

Similar to equation 8, in certain aspects, equation 17 is represented in Lie algebra form to enhance the smoothness of transformation. Substituting equation 14 into equation 17 yields:

$$e(c) = \sum_{i=1}^{4} \left( \begin{array}{l} \left\| P_s\left(\text{Exp}\left(\sum_{k=1}^{6} c^k V_k\right)\right) p_{s0}^i - \hat{p}_s^i \right\|^2 + \\ \left\| P_a\left(\text{Exp}\left(\sum_{k=1}^{6} c^k V_k\right)\right) p_{a0}^i - \hat{p}_a^i \right\|^2 + \\ \left\| P_c\left(\text{Exp}\left(\sum_{k=1}^{6} c^k V_k\right)\right) p_{c0}^i - \hat{p}_c^i \right\|^2 \end{array} \right) \quad \text{Equation 19}$$

The optimal $c^* \arg\min \{e(c)\}$ is obtained by solving equation 19 using the Gauss-Newton method.

Global Geometry Module for Spine Shape Registration

Global geometry module 414 performs the global shape registration for the detected vertebra landmarks. This module is built upon the 3D spine model and its shape recognition. The 3D spine model is formed by the combined local triplanar vertebra models and is abstracted as a pint-connected global model. Shape registration of the spine model provides a top-down point matching for the potential landmarks. The global module is described by three parts: the unification of triplanar models that forms the global spine, the vertebra parsing that removes outlier landmarks, and the non-rigid deformation of global spine model that conducts the shape registration.

Unification of Local Models

Similar to the generative model of the local triplanar model, the global spine model is described as a higher order generative model. In certain aspects, a graphical probability model is applied to formulate the higher order generative model. Similar to the compositional anatomic structure of the spine, the 3D model (without point abstraction) in a HDM is composed by the set of 3D triplanar vertebra models. The ith vertebra in the spine model is the local triplanar geometry model whose pose is $C_i$ and has triplanar appearance $\Gamma_i$: $C_i = (z_i, c_i), \Gamma_i = \{T_i^v\}$ where $z_i$ is the vertebra center location in $\mathbb{R}^3$, $c_i$ represents the 3D pose as in equation 19, and set $\{T_i^v\}$ contains the triplanar templates for $v \in \{$sagittal, axial, coronal$\}$. The whole spine global model which contains m vertebrae can be represented as a vertebra set $\{C_1, \ldots, C_m\}$. In certain aspects, landmark detection obtains a set of potential landmarks $\mathbb{R} \subset \mathcal{X}$. A detected landmark at $x \in \mathcal{X}$ whose configuration is described by its pose and appearance $C_x = (x, c_x)$, $\Pi_x = \{I_x^v\}$ where $\{I_x^v\}$ are the deformed planar patches around x from different image views v.

In certain aspects, each detected landmark x can only correspond to one triplanar model with one pose. In model-landmark matching, an observed local landmark and the planar image patches around the landmark are considered as being generated from one of the triplanar vertebrae models in the global spine model. A probability density function about landmark x can be constructed:

$$p(x) = p(\Pi_x, C_x; \{\Gamma_i, C_i\}) \quad \text{Equation 20:}$$

where $\{C_i\}_{i=1, \ldots, m}$ is the set of vertebrae in the global model. The formulation implies that the density function will increase when local landmark at $x \in \mathcal{X}$ is highly correlated to the global model. The correlation can be understood as a deformable matching when deformable model is driven by the force of likelihood. The driving force of x is tuned specifically for a single triplanar model in the global model. Equation 20 can be explicitly defined in prior-likelihood form:

$$p(\Pi_x, C_x; \{\Gamma_i, C_i\}) = p(\Pi_x, C_x | \{\Gamma_i, C_i\}) p(\{\Gamma_i, C_i\}) \quad \text{Equation 21:}$$

where $p(\{\Gamma_i, C_i\})$ represents the prior initialization of the global model. In certain aspects, a latent variable is introduced: L: $\mathcal{X} \to \{1, \ldots, m\}$ to represent the membership index of vertebra models ($\{\Gamma_1, C_i\}$) from the global spine, such that the landmark on x is considered as generated from the L(x)-th vertebra model. In addition, L satisfies $$L(z_{i+1}) = L(z)+1, i=1, \ldots, m-1$$

$$L(z_{i-1}) = L(z)-1, i=1, \ldots, m \quad \text{Equation 22:}$$

where $\{z_i\}$ belongs to the global model $\{C_1, \ldots, C_m\}$. Given an initialized global model, the planar appearances and pose of the local landmark at x are generated by a mixture model $$p(\Pi_x, C_x | \{\Gamma_i, C_i\}) = \Sigma_{L=1}^m p(L) p(\Pi_x L | \{\Gamma_i, C_i\})$$
$$p(C_x | L, \{C_i\}) \quad \text{Equation 23:}$$

where p(L) is the latent variable describing the association of current landmark and the specific vertebra model.

In the formulation of equation 23, p(L) can be defined as uniform distribution 1/m and the deformable matching will reduce to blind registration. Instead of uniform distribution, in certain aspects, p(L) can be defined as the confidence of local spatial compatibility where the explicit definition is defined below. The confidence is adaptive according to vertebra model type, so that some special landmarks can have stronger attraction to the corresponding vertebra models. The landmark-model correspondence of planar appearances and the correspondence of poses are defined respectively as $$p\left(\prod_x | L, \{\Gamma_i^v, C_i\}\right) = \prod_v p(I_x^v | L, \{T_i^v, a_i^v\}) = \quad \text{Equation 24}$$

$$\prod_v p(I_x^v | T_i^v, a_i^v) = \frac{1}{z_\Pi} \prod_v \exp(-\alpha \phi T_L^v(a_L^v))$$

and $$p(C_x | L, \{C_i\}) = p(x | L, \{z_i, c_i\}) p(c_x | L, \{c_i\}) \quad \text{Equation 25}$$

$$= p(x | L, \{z_i\}) \prod_v p(a_x^v | L, \{a_i^v\})$$

$$= p\left(x | z_L \prod_v \prod_{j \in \mathcal{N}(i) \cup i} p(a_x^v | a_i^v)\right)$$

$$= p\left(x | z_L \times \frac{1}{z_a} \prod_v \exp\left(-\gamma \sum_{j \in \mathcal{N}(i) \cup i} \psi(a_x^v, a_j^v)\right)\right)$$

where $\phi$ and $\psi$ are defined in equation 8. Thus, the local geometry alignment (equation 8) is integrated into the global model of equation 21, and the local alignment now contributes to the global deformable matching.

Since the global spine model is represented as the set of connected triplanar vertebra models, the deformation of the global model corresponds to the collaborated deformations of triplanar models which is highly complicated. The graphical probability model can not only unify the appearance-pose representations among local models, but can also unify the local and global deformation formulations in a single formulation. The interactions between global spine and local vertebra can be easily accomplished using this formulation.

Vertebra Parsing

Vertebra parsing is the verification for removing falsely detected landmarks using the spatial inter-vertebra correspondences. It reduces the ambiguity of spine shape registration. There are two spatial clues that help to verify the correct landmarks: 1) Pose compatibility of adjacent landmark. As the spine is a part-connected structure, the correct match of a landmark and a vertebra model suggests that the spatial organization of nearby landmarks should also be compatible with the organization of the adjacent vertebra models in the global spine model. Outliers can be easily removed by its spatial compatibility. 2) Anchor vertebra. The anchor vertebrae are the vertebrae whose appearances are significantly different from the other vertebra in the spine. These special vertebra are used to identify the spine section (lumbar or cervical) of the input data. In certain aspects, the anchor vertebrae used are (a) the S1 for identifying lumbar related sections; (b) the C1+C2 (combined as one model) for identifying cervical related sections.

The overall vertebra parsing is carried out as: Identify spine section by anchor vertebra and remove outliers that are not compatible with local spatial organization. Vertebra parsing is formulated in the form of graphical model of equation 20. Let p(L) represent the classification of landmark $x \in \mathcal{X}$ as vertebra $L(x) \in \{1, \ldots m\}$. L is considered a Markov random field (MRF) over $\mathcal{X}$ $$p(L) = \Pi_{x \in \mathcal{X}} p(L(x) | L(y)) \quad \text{Equation 26:}$$

where $\{L(y)\}_{y \in \mathcal{N}_k(x)}$ represents the labels assigned to a modified neighbor set $\mathcal{N}_k(x)$. Unlike the traditional definition of neighbor set $\mathcal{N}(x)$, $\mathcal{N}_k(x)$ is defined as $$\mathcal{N}_k(x) = \mathcal{N}(x + kR(x)d), k \in \{-K, \ldots, K\} \quad \text{Equation 27:}$$

where k>0 is an integer and $d \in \mathbb{R}^2$ is a unit vector. $\mathcal{N}_k$ is the neighbors of x obtained by shifting x with displacement d oriented by R(x), where R(x) is the planar pose obtained from equation 18. The potential landmark location is confirmed only if its $\mathcal{N}_{\pm 1}$ neighbors are in compatible locations.

The probability of p(L(x)|L(y)) is defined as:

$$p(L(x) | L(y)) = \frac{1}{z_L} \exp\left(p \sum_{k=-K}^K \sum_{y \in \mathcal{N}_k(x)} \delta(L(x)+k, L(y))\right) \quad \text{Equation 28}$$

where $\delta$ is the Kronecker delta function. The definition indicates the x can be labeled as the L(x)-th vertebra only if its shifted position y is a potential landmark labeled as L(x)+k. The parsing of L(x) is then done by maximizing the log-likelihood of equation 28, which, in certain aspects, can be implemented by a linear searching algorithm. The outliers are eliminated after parsing, leaving only the correct vertebra landmarks.

Registration for Spine Shape

The shape registration of spine model and detected landmarks are implemented by point-based registration. In this registration, each vertebra models in the spine model are abstracted as points to match the identified landmarks obtained from vertebra parsing. The registration is driven by minimizing point pair inter-distances modulated with landmark alignment and appearance matching. The deformation applied in our registration is inspired by coherence point drift (CPD).

As the registration is point-based, the explicit point correlation needs to be defined. Following the formulation of generative mixture mode in Equation 23, the explicit definition of $p(x|z_L)$ in Equation 25 becomes:

$$p(x\mid z_L) = \frac{1}{(2\pi\sigma^2)^{\frac{3}{2}}}\exp\left(-\frac{\|x-(z_L+v(z_L))\|^2}{2\sigma^2}\right) \quad \text{Equation 29}$$

where $v(z_L)$ is the displacement of the original vertebra location $z_L$. The likelihood above represents the attraction between x and $z_L$, which in certain aspects, can be understood as a Gaussian Mixture Model (GMM). A variation for the position $z_L+v(z_L)$ or for the standard deviation σ will cause the likelihood to change accordingly, which implies the mode of $z_L$ towards or away from x. The goal is then to search for the optimal v and σ. The objective function can be written as:

$$Q(v,\sigma) = -\log\prod_x p\left(\prod_x, C_x\mid\{\Gamma_i,C_i\}\right) \quad \text{Equation 30}$$

$$= \sum_x \log\sum_L p(L)p\left(\prod_x\mid L,\{\Gamma_i,C_i\}\right)p(C_x\mid\{C_i\})$$

$$= -\sum_x \log\sum_L \theta(x,L)p(x\mid z_L)$$

where $$\Theta(x,L)=p(L)p(\Pi_x\mid L,\{\Gamma_i,C_i\})\Pi_\nu\Pi_{j\in\mathcal{N}(i)\cup i}p(a_x^\nu,a_j^\nu) \quad \text{Equation 31:}$$

and p(L), $p(\Pi_x\mid L,\{\Gamma_i,C_i\})$, $p(a_x^\nu,a_j^\nu)$ an are defined in Equation 28, 24, and 25, respectively. In certain aspects, the objective function in Equation 30 can be minimized using the expectation-maximization (EM) algorithm, which iteratively updates the parameters in Equation 30 to solve v and σ. Using the EM algorithm formulation, Equation 30 can be reformulated as an equivalent minimization objective function:

$$Q=-\Sigma_x\Sigma_L p^{old}(z_L\mid x)\log(\Theta^{new}(x,L)p^{new}(x,z_L)) \quad \text{Equation 32:}$$

where $\Theta^{new}(\bullet,\bullet)$ and $p^{new}(\bullet,\bullet)$ represent the prior and likelihood in the M-step using the newly evaluated parameters. $p^{old}(z_L\mid x)$ is the posterior of the E-step which is evaluated using the old parameters. By minimizing Equation 32 instead of Equation 30 the same optimal v and σ can be obtained. From Equation 29 and Equation 25, Equation 32 can be revised as:

$$Q(v,\sigma) = \quad \text{Equation 33}$$

$$\sum_x\sum_L p^{old}(z_L\mid x)\left(\frac{\|x-z_L-v(z_L)\|^2}{2\sigma^2} - \log(\Theta(x,L))\right) +$$

$$\frac{3N_P}{2}\log\sigma^2$$

$$p^{old}(z_L\mid x) = \frac{\exp\left(-\frac{\|x-z_L-v^{old}(z_L)\|^2}{2(\sigma^{old})^2}\right)\Theta(x,L)}{\exp\left(-\frac{\|y-z_L-v^{old}(z_L)\|^2}{2(\sigma^{old})^2}\right)\Theta(y,L)}$$

where $N_p=\Sigma_x\Sigma_L p^{old}(z_L\mid x)$.

In certain aspects, the variance v is assumed to be smooth, so that different point x will not collapse and their velocity flow will not interfere with each other in deformation. In certain aspects, a coherence regularization term is added:

Equation 35:

$$Q(v,\sigma) = \sum_x\sum_L p^{old}(z_L\mid x)\left(\frac{\|x-z_L-v(z_L)\|^2}{2\sigma^2} - \log(\Theta(x,L))\right) +$$

$$\frac{3N_P}{2}\log\sigma^2 + \frac{\lambda}{2}\sum_x \|v(z_L)\|_H^2$$

where λ>0. $\|\bullet\|H$ is the norm for a Hilbert space H .

To obtain the optimal v, σ is fixed in Equation 35 then from the Euler-Lagrange equation:

$$\frac{1}{2\sigma^2\lambda}\sum_x\sum_L p^{old}(z_L\mid x)(x-z_L-v(z_L))\delta(y-z_L) = \quad \text{Equation 36}$$

$$\sum_{k=0}^\infty (-1)^k \beta_k D^{2k} v(y).$$

The solution is derived from the Green's function of the differential operator on the right side:

$$\frac{1}{2\sigma^2\lambda}\sum_x\sum_L p^{old}(z_L\mid x)(x-z_L-v(z_L))K(y,-z_L) \quad \text{Equation 37}$$

where K is the Green's function. σ can be obtained by choosing a Gaussian function for K and fix v:

$$\sigma^2 = \frac{1}{3N_P}\sum_{x\in X}\sum_L \|x-z_L-v(z_L)\|^2 \quad \text{Equation 38}$$

The updated v and σ are substituted in Equation 34 and then continue to compute the new v and σ in the next iteration.

In these examples, the machine readable instructions comprise a program for execution by a processor such as processor 512 shown in the example processor platform 500 discussed below in connection with FIG. 5. The program can be embodied in software stored on a tangible computer readable storage medium such as a CD-ROM, a floppy disk, a hard drive, a digital versatile disk (DVD), a BLU-RAY™ disk, or a memory associated with processor 512, but the entire program and/or parts thereof could alternatively be executed by a device other than processor 512 and/or embodied in firmware or dedicated hardware. Further, although the example program is described with reference to the flowchart illustrated in FIG. 4, many other methods of implementing the example multi-kernel learning can alternatively be used. For example, the order of execution of the blocks can be changed, and/or some of the blocks described can be changed, eliminated, or combined.

As mentioned above, the example processes of FIG. 4 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 4 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

V. COMPUTING DEVICE

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein may include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and may include volatile and non-volatile, removable and non-removable media for storage of electronic-formatted information such as computer readable program instructions or modules of instructions, data, etc. that may be stand-alone or as part of a computing device. Examples of computer readable storage medium or computer program products may include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein may include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 5:
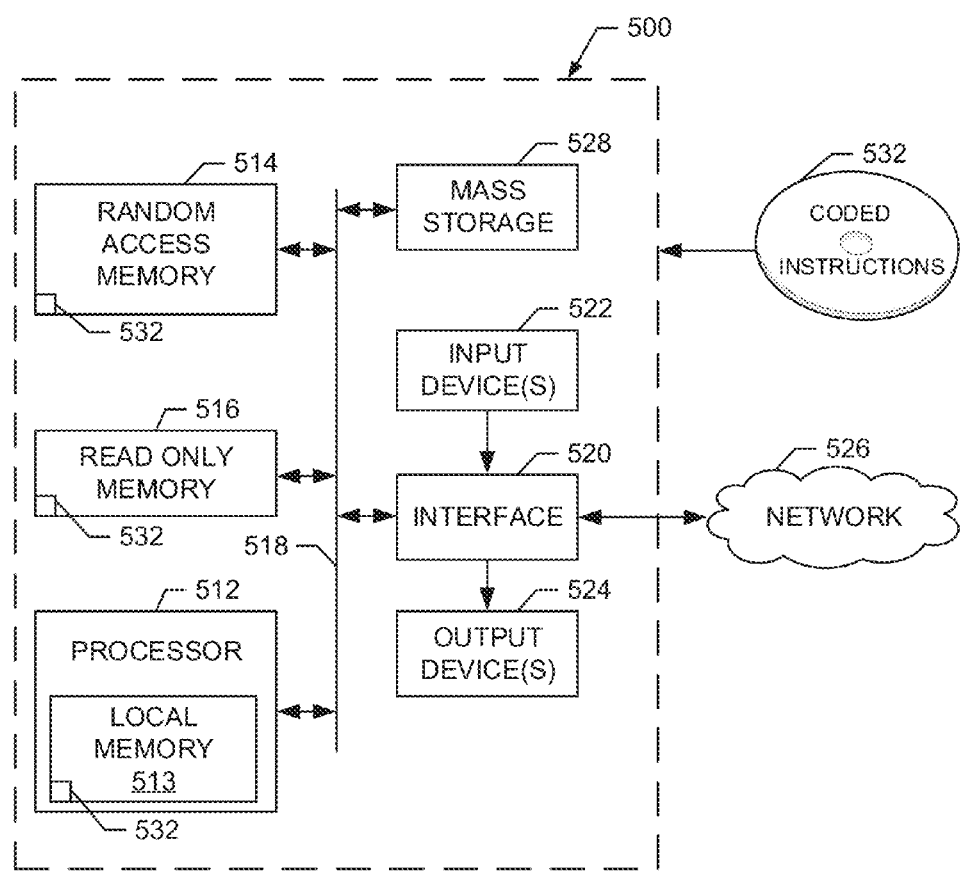
FIG. 5 shows a block diagram of an example processor system that can be used to implement systems and methods described herein.

FIG. 5 is a block diagram of an example processor platform 500 capable of executing the instructions of FIG. 4 to implement the example multi-modality vertebrae recognition engine of FIG. 3. The processor platform 500 can be, for example, a server, a personal computer, a mobile device (e.g., a cell phone, a smart phone, a tablet such as an IPAD™), a personal digital assistant (PDA), an Internet appliance, or any other type of computing device.

The processor platform 500 of the illustrated example includes a processor 512. Processor 512 of the illustrated example is hardware. For example, processor 512 can be implemented by one or more integrated circuits, logic circuits, microprocessors or controllers from any desired family or manufacturer.

Processor 512 of the illustrated example includes a local memory 513 (e.g., a cache). Processor 512 of the illustrated example is in communication with a main memory including a volatile memory 514 and a non-volatile memory 516 via a bus 518. Volatile memory 514 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 can be implemented by flash memory and/or any other desired type of memory device. Access to main memory 514, 516 is controlled by a memory controller.

Processor platform 500 of the illustrated example also includes an interface circuit 520. Interface circuit 520 can be implemented by any type of interface standard, such as an Ethernet interface, a universal serial bus (USB), and/or a PCI express interface.

In the illustrated example, one or more input devices 522 are connected to the interface circuit 520. Input device(s) 522 permit(s) a user to enter data and commands into processor 512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 524 are also connected to interface circuit 520 of the illustrated example. Output devices 524 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 520 of the illustrated example, thus, typically includes a graphics driver card, a graphics driver chip or a graphics driver processor.

Interface circuit 520 of the illustrated example also includes a communication device such as a transmitter, a receiver, a transceiver, a modem and/or network interface card to facilitate exchange of data with external machines (e.g., computing devices of any kind) via a network 526 (e.g., an Ethernet connection, a digital subscriber line (DSL), a telephone line, coaxial cable, a cellular telephone system, etc.).

Processor platform 500 of the illustrated example also includes one or more mass storage devices 528 for storing software and/or data. Examples of such mass storage devices 528 include floppy disk drives, hard drive disks, compact disk drives, Blu-ray disk drives, RAID systems, and digital versatile disk (DVD) drives.

Coded instructions 532 of FIG. 4 can be stored in mass storage device 528, in volatile memory 514, in the non-volatile memory 516, and/or on a removable tangible computer readable storage medium such as a CD or DVD.

VI. CONCLUSION

Thus, certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost.

Certain examples facilitate improved control over process. For example, certain example systems and methods provide the ability to perform automatic vertebra recognition to identify the global spine and local vertebra structural information such as spine shape, vertebra location and pose. Automatic spine recognition which supports quantitative measurement is essential in numerous spine related applications in orthopedics, neurology, and oncology. The task of automatic spine recognition is to extract the set of numerical parameters that can uniquely determine the global structure of the spine and certain local structures of the vertebrae. Currently, spine recognition is often simplified as vertebra detection, which extracts the locations and labels of the vertebrae in input images.

Certain examples leverage information technology infrastructure to standardize and centralize data across an organization. In certain examples, this includes accessing multiple systems from a single location, while allowing greater data consistency across the systems and users.

Technical effects of the subject matter described above may include, but is not limited to, providing systems and methods of automatic vertebra recognition to identify the global spine and local vertebra structural information such as spine shape, vertebra location and pose.

Moreover, the system and method of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer-implemented method to recognize one or more anatomic structures in digital images, the method comprising:
    loading a pre-computed 3D spine mesh model with reference data comprising prior geometric measurements of the human spine;
    receiving image data comprising one or more images of at least one anatomic structure;
    generating, using a processor, one or more planar vertebra appearance templates using said one or more images;
    identifying vertebrae landmarks using image feature matching between said one or more images and said one or more planar vertebra appearance templates;
    computing, using a processor, the spine shape by aligning said vertebrae landmarks with said pre-computed 3D spine mesh model;
    identifying the orientation and dimension of said one or more anatomic structures using a triplanar model and group-wise registration;
    computing, using a processor, a 3D spine model using a hierarchical deformable model, said planar vertebra templates, said vertebra landmarks, and said spine shape; and
    display said computed 3D model of the spine on said computer.

2. The computer-implemented method of claim 1, wherein said computed 3D spine model comprises:
    identifying local and global spine structures;
    identifying spine shape, and
    extracting vertebra information comprising vertebra locations, labels and poses.

3. The computer-implemented method of claim 1, wherein generating said 3D spine model comprises:
    using images comprising at least one anatomic structure, from at least one anatomic plane, from at least one imaging modality.

4. The computer-implemented method of claim 2, wherein the said extracted vertebra information and said identified spine shape are used for diagnostic purposes.

5. The computer-implemented method of claim 1, wherein the dimensions and orientations of local vertebra parts can be adjusted by a human user.

6. A computer storage device including program instructions for execution by a computing device to perform:
    loading a pre-computed 3D spine mesh model with reference data comprising prior geometric measurements of the human spine;
    receiving image data comprising one or more images of at least one anatomic structure;
    generating, using a processor, one or more planar vertebra appearance templates using said one or more images;
    identifying vertebrae landmarks using image feature matching between said one or more images and said one or more planar vertebra appearance templates;
    computing, using a processor, the spine shape by aligning said vertebrae landmarks with said pre-computed 3D spine mesh model;

identifying the orientation and dimension of said one or more anatomic structures using a triplanar model and group-wise registration;

computing, using a processor, a 3D spine model using a hierarchical deformable model, said planar vertebra templates, said vertebra landmarks, and said spine shape; and display said computed 3D model of the spine on said computer.

7. The computer storage device of claim 6, further including program instructions for execution by said computing device to perform:

using said 3D spine model to:

identify local and global spine structures;

identify spine shape, and extract vertebra information comprising vertebra locations, labels and poses.

8. The computer storage device of claim 6, further including program instructions for execution by said computing device to perform:

generating the 3D spine model comprises using images comprising at least one anatomic structure, from at least one anatomic plane, from at least one imaging modality.

9. The computer storage device of claim 7, further including program instructions for execution by said computing device to perform:

extracting vertebra information and said identified spine shape to be used for diagnostic purposes.

10. The computer storage device of claim 6, further including program instructions for execution by said computing device to perform:

allowing a human user to adjust the dimensions and orientations of local vertebra parts.

11. A system comprising a processor, the processor configured to execute computer program instructions to:

load a pre-computed 3D spine mesh model with reference data comprising prior geometric measurements of the human spine;

receive image data comprising one or more images of at least one anatomic structure;

generate, using a processor, one or more planar vertebra appearance templates using said one or more images;

identify vertebrae landmarks using image feature matching between said one or more images and said one or more planar vertebra appearance templates;

compute, using a processor, the spine shape by aligning said vertebrae landmarks with said pre-computed 3D spine mesh model;

identify the orientation and dimension of said one or more anatomic structures using a triplanar model and group-wise registration;

compute, using a processor, a 3D spine model using a hierarchical deformable model, said planar vertebra templates, said vertebra landmarks, and said spine shape; and display said computed 3D model of the spine on said computer.

12. The system of claim 11, wherein the system further comprises:

identifying local and global spine structures;

identifying spine shape, and extracting vertebra information comprising vertebra locations, labels and poses.

13. The system of claim 11, wherein the system further comprises:

generating said 3D spine model using images comprising at least one anatomic structure, from at least one anatomic plane, from at least one imaging modality.

14. The system of claim 12, wherein the system further comprises:

extracting said vertebra information and said identified spine shape are used for diagnostic purposes.

15. The system of claim 11, wherein the system further comprises:

allowing a human user to adjust the dimensions and orientations of local vertebra parts.

* * * * *